(12) United States Patent
Russak (10) Patent No.: US 11,072,821 B2
(45) Date of Patent: *Jul. 27, 2021

(54) IDENTIFYING TRANSITION POINTS IN CHEMICAL REACTIONS

(75) Inventor: Ze'ev Russak, Ramat Gan (IL)

(73) Assignee: AZURE VAULT LTD., Ramat Gan (IL)

(*) Notice: Subject to any disclaimer, the term of this patent is extended or adjusted under 35 U.S.C. 154(b) by 600 days.

This patent is subject to a terminal disclaimer.

(21) Appl. No.: 13/394,440

(22) PCT Filed: Sep. 12, 2009

(86) PCT No.: PCT/IB2009/053997
§ 371 (c)(1),
(2), (4) Date: Mar. 6, 2012

(87) PCT Pub. No.: WO2011/030186
PCT Pub. Date: Mar. 17, 2011

(65) Prior Publication Data
US 2012/0166100 A1    Jun. 28, 2012

(51) Int. Cl.
*C12Q 1/6851* (2018.01)
*G16C 20/10* (2019.01)
*G16C 20/70* (2019.01)

(52) U.S. Cl.
CPC .......... *C12Q 1/6851* (2013.01); *G16C 20/10* (2019.02); *G16C 20/70* (2019.02)

(58) Field of Classification Search
None
See application file for complete search history.

(56) References Cited

U.S. PATENT DOCUMENTS

| | | | |
|---|---|---|---|
| 6,120,741 A * | 9/2000 | Jacquault | B01J 19/126 422/199 |
| 6,503,720 B2 | 1/2003 | Wittwer et al. | |
| 6,783,934 B1 | 8/2004 | McMillan et al. | |
| 6,911,327 B2 | 6/2005 | McMillan et al. | |
| 2003/0194122 A1 | 10/2003 | Stone et al. | |
| 2003/0211630 A1 * | 11/2003 | Richards | G01N 1/30 436/174 |
| 2006/0224330 A1 | 10/2006 | Kurnik et al. | |
| 2007/0057159 A1 * | 3/2007 | Hing | G01J 3/2803 250/214 R |
| 2007/0073490 A1 | 3/2007 | Kurnik et al. | |
| 2007/0124088 A1 | 5/2007 | Woo et al. | |
| 2007/0129899 A1 | 6/2007 | Ward et al. | |
| 2007/0143385 A1 * | 6/2007 | Kurnik | G06F 17/10 708/290 |
| 2007/0148632 A1 | 6/2007 | Kurnik et al. | |
| 2007/0284241 A1 * | 12/2007 | Kibar | B01J 19/0006 204/157.15 |
| 2007/0292941 A1 * | 12/2007 | Handique | B01L 3/5027 435/288.7 |
| 2009/0119020 A1 | 5/2009 | Kurnik et al. | |
| 2010/0070190 A1 | 3/2010 | Lerner | |

FOREIGN PATENT DOCUMENTS

| | | |
|---|---|---|
| JP | 2007-128483 | 5/2007 |
| WO | WO/2003/029924 | 4/2003 |

OTHER PUBLICATIONS

"OriginLab® Origin: Fitting Multiple Peaks with Peak Analyzer", http://youtu.be/FrpU662NAkl, uploaded Jul. 28, 2009.*
K. Connors Chemical Kinetics: The Study of Reaction Rates in Solution, 1990.*
Stowers et al. J Biomed Sci Eng.,3(5): 459-469, 2010.*
International Search Report and Written Opinion dated May 19, 2010 in international application No. PCT/IB2009/053997.
International Preliminary Report on Patentability dated Sep. 30, 2011 in international application No. PCT/IB2009/053997.
Lee et al., "ReasonSense?: simple linear fluorescent probes for quantitative homogenous rapid polymerase chain reaction." Analytica Chimica Acta 2002, available on line Nov. 28, 2001, vol. 457, pp. 61-70.
Brechtbuehl et al., "A rapid real-time quantitative polymerase chain reaction for hepatitis B virus", Journal of Virological Methods, 2001,available on line Apr. 10, 2001, vol. 93, pp. 105-113.
Schechtman, "Inference in Two-Phase Regression: A Simulation study with Non-normal Observation", Journal of Statistical Computation and Simulation, vol. 17, issue 3, 1983 (pp. 223-229).
Brechtbuehl et al., A rapid real-time quantitative polymerase chain reaction for hepatitis B virus. J Virol Methods. Apr. 2001;93(1-2):105-113.
Lee et al., ResonSense: simple linear fluorescent probes for quantitative homogenous rapid polymerase chain reaction. Analytica Chimica Acta 2002,;457:61-70.
Palais and Wittwer, Mathematical Algorithms for High-Resolution DNA Melting Analysis. Methods Enzymol. 2009;454:323-343.

* cited by examiner

*Primary Examiner* — Michael L Borin
(74) *Attorney, Agent, or Firm* — Acuity Law Group, PC; Michael A. Whittaker (57) ABSTRACT

An apparatus for identifying transition points in a chemical reaction, the apparatus comprising: a property value receiver, configured to receive a plurality of values of a physical property of the chemical reaction, a linear function calculator, associated with the property value receiver, configured to calculate a linear function connecting two of the received values, the two values pertaining to a start and end of a time period, a difference calculator, associated with the linear function calculator, configured to calculate a difference between the linear function and a plurality of the received values pertaining to the time period, and a transition point identifier, associated with the difference calculator, configured to identify at least one transition point of the chemical reaction, using the calculated difference.

26 Claims, 8 Drawing Sheets

Fig. 5

IDENTIFYING TRANSITION POINTS IN CHEMICAL REACTIONS

FIELD AND BACKGROUND OF THE INVENTION

This application is a national phase of International Patent Application No. PCT/IB2009/053997, filed Sep. 12, 2009.

The present invention relates to analyzing, monitoring and controlling chemical reactions and, more particularly, but not exclusively to systems and method for identifying transition points in chemical reactions such as PCR (Polymerase Chain Reaction).

Chemical reaction may need to be characterized in real-time.

For example, detection and quantification of a molecule in a chemical reaction may be required to take place as the reaction progresses, in order to characterise the pattern of the reaction, take certain steps when the reaction moves into a new phase, etc.

Of special interest are a point of exponential growth of the chemical reaction product and a point where growth of the product begins to slow to a halt, also referred to as elbow points. The elbow points may be used to determine whether any reaction products have been produced. The magnitude of the reaction may be determined using a measured physical property of the reaction, say photometric measurements between the elbow points, as described in further detail hereinbelow.

One widely used and well-established laboratory technique is Polymerase Chain Reaction (PCR).

In PCR, the polymerase enzyme attaches to a target DNA sequence and replicates it exactly along with its containing chromosome or DNA strand. If the target DNA sequence is not present or for some reason is unavailable for attachment to the PCR enzyme, no replication of DNA takes place. This procedure is repeated many times in a PCR reaction instrument. Thus, the target DNA sequence, as well as overall DNA concentration, is amplified to microgram levels to allow for accurate detection and data analysis.

Quantitative Fluorescent Polymerase Chain Reaction (QF-PCR) is a widely used PCR method. QF-PCR is commonly used for diagnosis and research in fields such as disease (infectious or inherited), blood screenings, histology, oncology, tissue typing and drug discovery.

In QF-PCR, phosphate groups are introduced into the PCR reaction in order to mark the replicated molecules for purposes of real-time detection and quantification.

The two common methods for QF-PCR are: 1) Fluorescent dyes that intercalate with double-stranded DNA and 2) Modified DNA probes that fluoresce only when hybridised with the target DNA sequence, as known in the art.

The latter method is more sensitive and therefore more reliable and accurate, it also allows for real-time quantification of multiple DNA sequences using differently coloured probes.

The data received is in the form of fluorescent intensity, called FI.

The FI data may be represented using a graph. The shape of the graph may be either linear (if a target DNA sequence was not found or not amplified) or appear to be a sigmoid curve (if the target sequence DNA was amplified).

In case of presence of the target DNA sequence, there arises a need to identify the point where amplification of the DNA sequence begins to take place, also referred to as the threshold point or $C_T$. However, the FI data in the threshold's region usually has a low Signal to Noise Ratio (SNR).

Consequently, determining $C_T$ with a high degree of accuracy requires a method or a combination of methods for refining the FI data.

In photometric methods such as QF-PCR, photometry is utilised for real-time detection and quantification of a reaction product.

In order to determine whether a) any reaction products have been produced, and b) the magnitude of production, targeted photoactive probes are utilised in the chemical reaction, to produce a photometric effect (i.e. light) detectable by an optical sensor. The magnitude of the production is derived from data pertaining to the intensity of the photometric effect.

Determining whether any reaction products have been produced, and the magnitude the production accurately is limited by the amount of noise in the recorded photometric data. The noise may originate from chemical sources, such as the reaction mix, as well as from electronic sources, such as the instrument used for light detection.

Several traditional methods have been used to determine time points of exponential growth on a graph representing a quantitative measurement of a chemical reaction over time.

One traditional method involves an n-derivative of light intensity used to determine time periods of exponential growth.

International Patent Application No.: PCT/US2002/031144, to Taylor et al., published on Apr. 10, 2003, entitled "Adaptive baseline algorithm for quantitative", describes baseline subtraction algorithms developed to reduce tube-to-tube and cycle-to-cycle variabilities during real time PCR amplification. Particularly, Taylor describes an algorithm for determining a threshold cycle, for detection of an amplified nucleic acid production.

U.S. patent application Ser. No. 11/645,964, to Woo et al., filed on Dec. 27, 2006, entitled "Automatic threshold setting and baseline determination for real-time PCR", discloses a method which involves a base-lining operation, for identifying the bounds of a baseline region and performing a linear interpolation to identify the characteristic equation defining the baseline.

US Patent Publication No. 20070148632, to Kurnik et al., describes Systems and methods for determining characteristic transition values such as elbow values in sigmoid or growth-type curves, utilizing a Levenberg-Marquardt (LM) regression process.

U.S. patent application Ser. No. 11/861,188, to Kurnik et al., filed on Sep. 25, 2007, entitled "PCR elbow determination using curvature analysis of a double sigmoid", describes a method utilizing a first or second degree polynomial curve that fits the a growth type curve, and determination of a statistical significance value for the curve fit. The significance value indicates whether the data represents significant or valid growth.

Some traditional methods based on linear regression, are used to determine the time point where growth in light intensity changes from linear to exponential. Typically, the linear regression based methods include prior setting of a threshold for intensity, to determine the start of exponential growth.

A particular method involving two-phase regression is described in an article by Edna Schechtman, published in the Journal of Statistical Computation and Simulation, volume 17, issue 3, 1983 (pages 223-229), entitled "Inference in Two-Phase Regression: A Simulation study with Non-normal Observation".

Some currently used methods involve converting data into a graph image and rotating the image.

In a one example, U.S. patent application Ser. No. 11/349,538, to Kurnik, filed on Feb. 6, 2006, entitled "PCR elbow determination by rotational transform after zero slope alignment", describes PCR data set visualization in a two-dimensional plot of fluorescence intensity vs. cycle number. Then, the PCR data set is adjusted to have a zero slope.

In a second example, Japanese Patent Publication No. 2007128483, to Kurnik, published on May 24, 2007, entitled "PCR elbow determination by rotational transform", describes a rotation transform application to a modified data set, to rotate the data about a defined coordinate such as the origin, so that the data point representing the Ct value may become a minimum or a maximum along the intensity axis. The data point representing the elbow or Ct value of the curve is identified, and this data point is then reversed back and the cycle number of the data point is displayed.

U.S. patent application Ser. No. 11/423,377, to Kurnik, filed on September 2006, entitled "CT determination by cluster analysis with variable cluster endpoint", describes PCR data set visualized in a two-dimensional plot of fluorescence intensity (y-axis) vs. cycle number (x-axis). Then, the points of the plot are clustered. Using the identified clusters, a linear slope of each of the clusters is determined and the data point representing the elbow or Ct value of the PCR curve is identified as an end point of one of the identified clusters.

Other Methods, such as the one disclosed by Wittwer et al., in U.S. Pat. No. 6,503,720, combine two or more of the methods described hereinabove.

SUMMARY OF THE INVENTION

According to one aspect of the present invention there is provided an apparatus for identifying transition points in a chemical reaction, the apparatus comprising: a property value receiver, configured to receive a plurality of values of a physical property of the chemical reaction, a linear function calculator, associated with the property value receiver, configured to calculate a linear function connecting two of the received values, the two values pertaining to a start and end of a time period, a difference calculator, associated with the linear function calculator, configured to calculate a difference between the linear function and a plurality of the received values pertaining to the time period, and a transition point identifier, associated with the difference calculator, configured to identify at least one transition point of the chemical reaction, using the calculated difference.

According to a second aspect of the present invention there is provided a computer implemented method for identifying transition points in a chemical reaction, the method comprising steps the computer is programmed to perform, the steps comprising: a) receiving a plurality of values of a physical property of the chemical reaction, b) calculating a linear function connecting two of the received values, the two values pertaining to a start and end of a time period, c) calculating a difference between the linear function and a plurality of the received values pertaining to the time period, and d) identifying at least one transition point of the chemical reaction, using the calculated difference.

According to a third aspect of the present invention there is provided a computer readable medium storing computer executable instructions for performing steps of identifying transition points in a chemical reaction, the steps comprising: a) receiving a plurality of values of a physical property of the chemical reaction, b) calculating a linear function connecting two of the received values, the two values pertaining to a start and end of a time period, c) calculating a difference between the linear function and a plurality of the received values pertaining to the time period, and d) identifying at least one transition point of the chemical reaction, using the calculated difference.

According to a fourth aspect of the present invention there is provided a system for identifying transition points in a chemical reaction, the apparatus comprising: a chemical reaction apparatus, comprising at least one sensor configured to measure a plurality of values of a physical property of a chemical reaction, a property value receiver, associated with the chemical reaction apparatus, configured to receive the plurality of values of the physical property of the chemical reaction, a linear function calculator, associated with the property value receiver, configured to calculate a linear function connecting two of the received values, the two values pertaining to a start and end of a time period, a difference calculator, associated with the linear function calculator, configured to calculate a difference between the linear function and a plurality of the received values pertaining to the time period, and a transition point identifier, associated with the difference calculator, configured to identify at least one transition point of the chemical reaction, using the calculated difference.

Unless otherwise defined, all technical and scientific terms used herein have the same meaning as commonly understood by one of ordinary skill in the art to which this invention belongs. The materials, methods, and examples provided herein are illustrative only and not intended to be limiting.

Implementation of the method and system of the present invention involves performing or completing certain selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. The description taken with the drawings making apparent to those skilled in the art how the several forms of the invention may be embodied in practice.

In the drawings.

DESCRIPTION OF THE PREFERRED EMBODIMENTS

The present embodiments comprise a system and method for identifying transition points in a chemical reaction.

For example, a point of exponential growth of the chemical reaction's product and a point where growth of the product begins to slow to a halt are referred to as elbow points. The elbow points may be used to determine whether any reaction products have been produced, as well as to determine the magnitude of the chemical reaction, as described in further detail hereinabove.

According to an exemplary embodiment of the present invention, one or more transition points of a chemical reaction are identified, using a linear function.

The linear function connects two values of a physical property of the chemical reaction, say photometric values measured by sensors installed in proximity of a PCR reaction chamber, during a PCR process. The two values pertain to a start and an end of a time period of the chemical reaction, respectively.

In order to identify the transition points, there is calculated a difference between the linear function and values of the physical property between the two values connected by the linear function (i.e. values measured between the start and end of the time period).

The calculated difference serves to emphasize phase transitions of the chemical reaction, which are non-linear, and are usually substantially exponential.

The phase transitions are emphasized since the linear function's slope represents a nearly average rate of the chemical reaction during the time period between the two points that the linear function connects.

That is to say that a comparison with the linear function helps identify the transition points of the chemical reaction. The transition points are thus characterized by a reaction rate which substantially deviates from the nearly average rate of the chemical reaction, as represented by the slope of the calculated linear function.

Having identified the transition point(s) of the chemical reaction, a system according to an exemplary embodiment, may provide a user (say a laboratory technician who operates a PCR Apparatus) with monitoring data based on the identified transition point(s).

The system according to an exemplary embodiment, may further initiate a control operation (say cooling of a chamber where the chemical reaction takes place) upon identifying the transition point(s), etc., as described in further detail hereinbelow.

The principles and operation of a system and method according to the present invention may be better understood with reference to the drawings and accompanying description.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Figure 1:
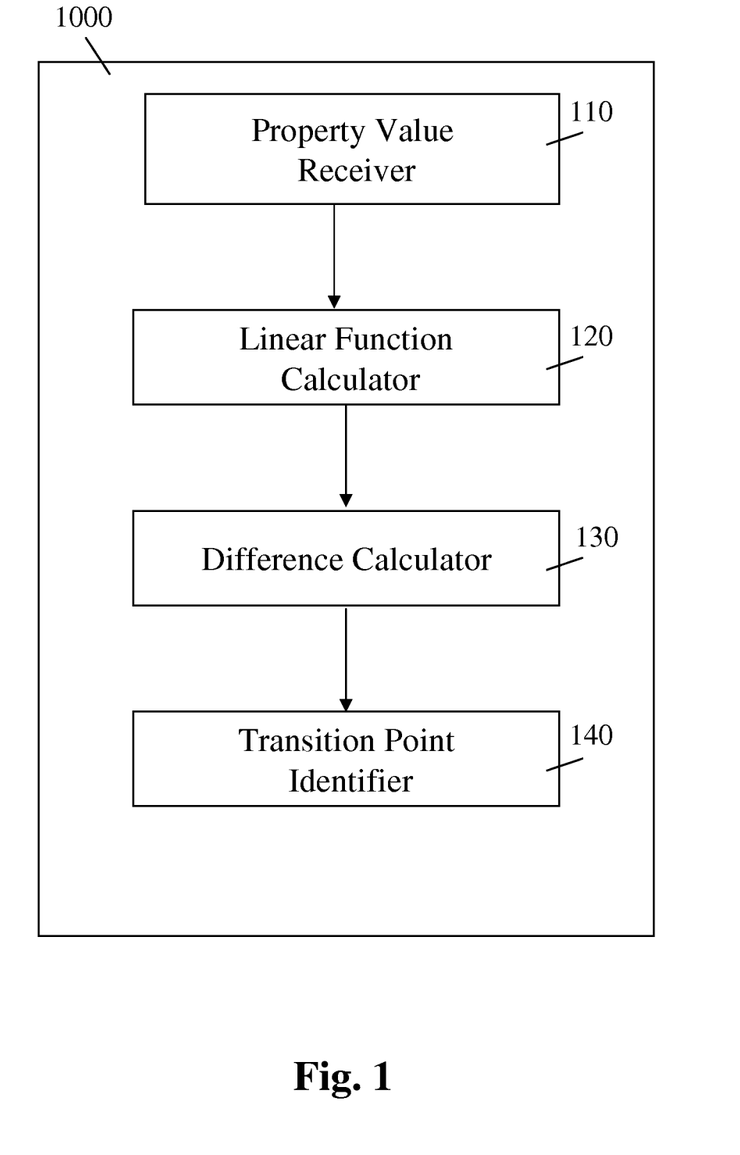
FIG. 1 is a block diagram schematically illustrating an apparatus for identifying transition points in a chemical reaction, according to an exemplary embodiment of the present invention.

Reference is now made to FIG. 1, which is a block diagram schematically illustrating an apparatus for identifying transition points in a chemical reaction, according to an exemplary embodiment of the present invention.

Apparatus 1000 for identifying transition points in a chemical reaction may be implemented using electric circuits, computer instructions, etc. The apparatus 1000 may be implemented on a dedicated computer, on a computer chip connectable to a laboratory device (say to a PCR apparatus, as known in the art) or installable thereon, on a computerized controller (say a computerized controller used in a chemical factory), etc.

Optionally, the chemical reaction is a Polymerase Chain Reaction (PCR), say a Quantitative Fluorescent Polymerase Chain Reaction (QF-PCR).

The apparatus 1000 includes a property value receiver 110.

The property value receiver 110 receives values of a physical property of the chemical reaction.

Optionally, the property value receiver 110 receives the physical property values from thermometric sensors installed inside a chamber where the chemical reaction takes place, from photometric sensors deployed in proximity to the chamber, or from other devices, as described in further detail hereinbelow.

For example, the chemical reaction may be a Quantitative Fluorescent Polymerase Chain Reaction (QF-PCR). The Quantitative Fluorescent Polymerase Chain Reaction is subjected to photometric measurements of light emitted from the QF-PCR reaction chamber, during the chemical reaction inside the QF-PCR chamber. The photometric measurement's values are then input to the property value receiver 110.

Optionally, the apparatus 1000 further includes one or more photometric measurement devices, say photo sensors installed in proximity to a chamber where the chemical reaction takes place. The photometric measurement devices are in communication with the property value receiver 110, for providing the property value receiver 110 with the values, as measured by the photometric measurement devices while the chemical reaction progresses.

The apparatus 1000 further includes a linear function calculator 120.

The linear function calculator 120 is in communication with the property value receiver 110.

The linear function calculator 120 calculates a linear function connecting two of the received values. The two values pertain to a start and end of a time period, as described in further detail hereinbelow.

The time period may be a time period the chemical reaction is supposed to last for, a time period when a part of the chemical reaction takes place, a time period long enough for the reaction to happen, a time period spanning several cycles of the chemical reaction, etc.

Optionally, the linear function calculator 120 further allows a user of the apparatus 1000, to define the start and end of the time period, say by inputting data defining the time period in absolute (say from 10:00 PM to 10:15 PM) or relative (say 15 minutes from start) terms.

The apparatus 1000 further includes a difference calculator 130, in communication with the linear function calculator 120.

The difference calculator 130 calculates a difference between the linear function and two (or more) of the received values that pertain to the time period. For example, the difference calculator 130 may calculate a differences between the linear function and a curve based on the receive values, over a time period of the chemical reaction (or a segment thereof), as described in further detail hereinbelow.

Apparatus 1000 further includes a transition point identifier 140, in communication with the difference calculator 130.

The transition point identifier 140 identifies one or more transition points of the chemical reaction, using the calculated difference, as described in further detail hereinbelow. For example, the transition point identifier 140 may identify the transition points, by finding the points where the difference between the linear function and the received values is maximal, minimal, etc.

Optionally, at least one of the transition points identified by the transition point identifier 140 is a point in time of the chemical reaction, when the value of the physical property starts increasing substantially exponentially.

Optionally, at least one of the transition points identified by the transition point identifier 140 is a point in time of the chemical reaction, when the value of the physical property stops increasing substantially exponentially.

Optionally, at least one of the transition points identified by the transition point identifier 140 is a point in time of the chemical reaction, when the value of the physical property starts decreasing substantially exponentially.

Optionally, at least one of the transition points identified by the transition point identifier 140 is a point in time of the chemical reaction, when the value of the physical property stops decreasing substantially exponentially.

Optionally, the apparatus 1000 also includes a phase indicator, in communication with the transition point identifier 140.

Optionally, when the transition point is identified, the phase indicator indicates a beginning of a phase of the chemical reaction, an end of a phase of the chemical reaction, an end of a preliminary stabilization phase of the chemical reaction, or any combination thereof.

Optionally, the apparatus 1000 further includes a control operation initiator, in communication with the transition point identifier 140.

When the transition point is identified, the control operation initiator initiates a control operation. The control operation may include, but is not limited to: initiating cooling of a chamber where the chemical reaction takes place, opening of a pressure valve of a reaction chamber, instructing a PCR Robot to stop rotating, etc., as known in the art.

Optionally, the apparatus 1000 further includes a monitoring data generator, in communication with the transition point identifier 140, as described in further detail hereinbelow.

The monitoring data generator generates monitoring data based on the identified transition point(s).

Optionally, the monitoring data generator further presents the generated data to a user, say using a computer screen, an SMS (Short Messages Service) message on a cellular phone used by the user, a message on a portable computer device such as a personal digital assistant (PDA), or a notebook computer, etc.

Figure 2:
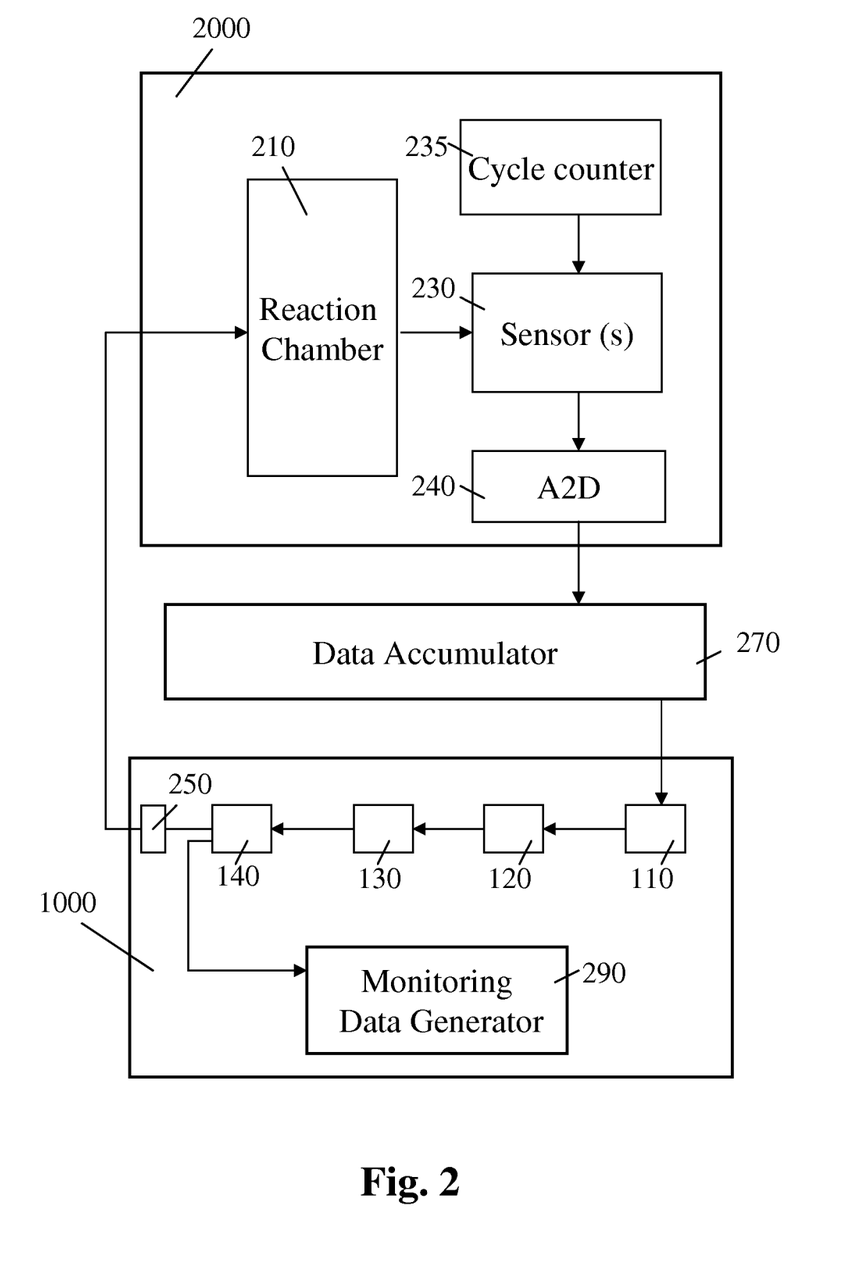
FIG. 2 is a block diagram schematically illustrating a system for identifying transition points in a chemical reaction, according to an exemplary embodiment of the present invention.

Reference is now made to FIG. 2, which is a block diagram schematically illustrating a system for identifying transition points in a chemical reaction, according to an exemplary embodiment of the present invention.

A system according to an exemplary embodiment of the present invention includes a chemical reaction apparatus 2000.

Optionally, the chemical reaction apparatus 2000 includes a reaction chamber 210, where a chemical reaction (say PCR) takes place.

Optionally, the chemical reaction apparatus 2000 further includes one or more sensors 230, for measuring values of a physical property of the chemical reaction.

For example, the sensors 230 may be photometric sensors installed in proximity of the reaction chamber 210. The photometric sensors measure intensity of light emitted from the reaction chamber 210, as the chemical reactions progresses.

The photometric sensors measure the emission of light from the reaction chamber, using standard fluorescence methods, as known in the art.

The chemical reaction apparatus 2000 may further include a cycle counter 235, connected to the sensors 230. The cycle counter 235 instructs the sensors 230 to take measurement of the physical property, say once in an interval of time. Optionally, the interval of time is predefined by a user, as known in the art.

The chemical reaction apparatus 2000 may further include an Analog-to-Digital (A2D) converter 240, connected to the sensors 230. The Analog-to-Digital (A2D) converter 240 converts the measured values of the physical property of the chemical reaction to a digital format.

The System of FIG. 2 further includes a data accumulator 270, in communication with the A2D converter 240.

The data accumulator 270 receives the measured values from the A2D converter 240, and stores the measured values.

The data accumulator 270 may include, but is not limited to a CD-ROM, a Flash Memory, a RAM (Random Access Memory), etc., as known in the art.

The system may further include apparatus 1000, as described in further detail hereinabove.

Apparatus 1000 may be implemented using electric circuits, computer instructions, etc. The apparatus 1000 may be implemented on a dedicated computer, on a computer chip connected to the chemical reaction apparatus 2000 or installed thereon, on a computerized controller connected to the chemical reaction apparatus 2000 or installed thereon, etc.

Optionally, the chemical reaction is a Polymerase Chain Reaction (PCR), say a Quantitative Fluorescent Polymerase Chain Reaction (QF-PCR), as described in further detail hereinabove.

Apparatus 1000 includes a property value receiver 110, in communication with the data accumulator 270.

The property value receiver 110 receives values of a physical property of the chemical reaction, from the data accumulator 270, as described in further detail hereinabove.

The apparatus 1000 further includes a linear function calculator 120.

The linear function calculator 120 is in communication with the property value receiver 110.

The linear function calculator 120 calculates a linear function connecting two of the received values. The two values pertain to a start and end of a time period, as described in further detail hereinbelow.

The time period may be a time period the chemical reaction is supposed to last for, a time period when a part of the chemical reaction takes place, a time period long enough for the reaction to happen, a time period spanning several cycles of the chemical reaction, etc.

Optionally, the linear function calculator 120 further allows a user of the apparatus 1000, to define the start and end of the time period, say by inputting data defining the time period, as described in further detail hereinabove.

The apparatus 1000 further includes a difference calculator 130, in communication with the linear function calculator 120.

The difference calculator 130 calculates a difference between the linear function and two (or more) of the received values that pertain to the time period. For example, the difference calculator 130 may calculate a differences between the linear function and a curve based on the receive values, over a time period of the chemical reaction (or a segment thereof), as described in further detail hereinbelow.

Apparatus 1000 further includes a transition point identifier 140, in communication with the difference calculator 130.

The transition point identifier 140 identifies one or more transition points of the chemical reaction, using the calculated difference, as described in further detail hereinbelow. For example, the transition point identifier 140 may identify the transition points, by finding the points where the difference between the linear function and the received values is maximal, minimal, etc.

Optionally, at least one of the transition points identified by the transition point identifier 140 is a point in time of the chemical reaction, when the value of the physical property starts increasing substantially exponentially.

Optionally, at least one of the transition points identified by the transition point identifier 140 is a point in time of the chemical reaction, when the value of the physical property stops increasing substantially exponentially.

Optionally, at least one of the transition points identified by the transition point identifier 140 is a point in time of the chemical reaction, when the value of the physical property starts decreasing substantially exponentially.

Optionally, at least one of the transition points identified by the transition point identifier 140 is a point in time of the chemical reaction, when the value of the physical property stops decreasing substantially exponentially.

Optionally, the apparatus 1000 further includes a control operation initiator 250, in communication with the transition point identifier 140.

When the transition point is identified, the control operation initiator 250 initiates a control operation. The control operation may include, but is not limited to:

initiating cooling of a chamber 210 where the chemical reaction takes place, opening of a pressure valve of the reaction chamber 210, instructing a PCR Robot to stop rotating, etc., as known in the art.

Optionally, the apparatus 1000 further includes a monitoring data generator 290, in communication with the transition point identifier 140. The monitoring data generator 290 generates monitoring data based on the identified transition point.

Optionally, the monitoring data generator 290 further presents the generated data to a user, say using a computer screen, an SMS (Short Messages Service) message on a cellular phone used by the user, a message on a portable computer device such as a personal digital assistant (PDA), or a notebook computer, etc.

Optionally, the monitoring data generator 290 further provides decision support services to the user (say by presenting the generated data to the user in a spreadsheet format such as a Microsoft© Excel spreadsheet).

Figure 3:
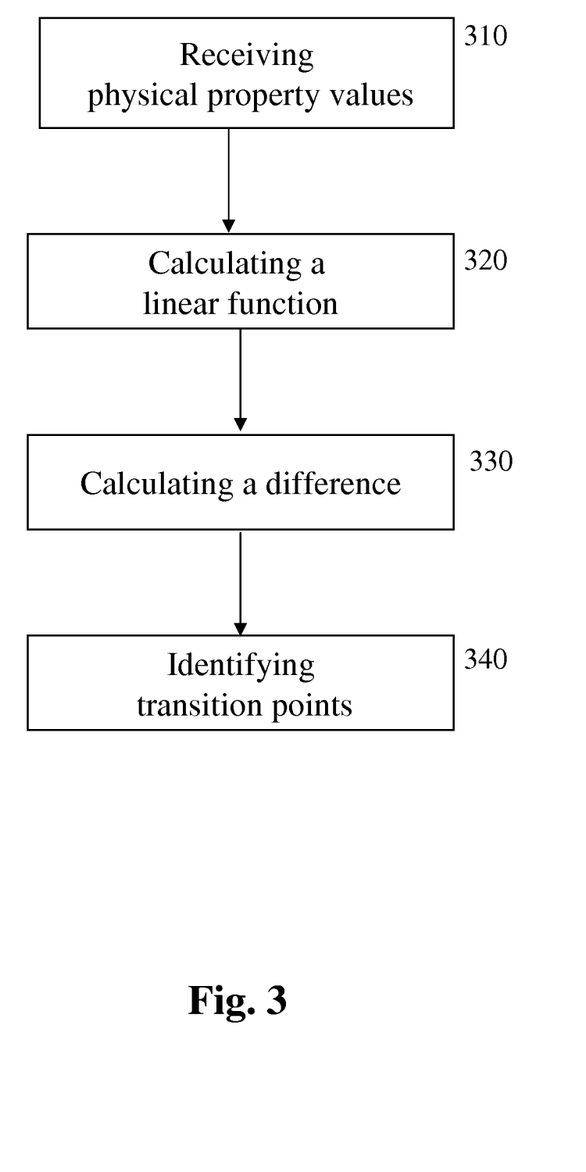
FIG. 3 is a flowchart schematically illustrating a method for identifying transition points in a chemical reaction, according to an exemplary embodiment of the present invention.

Reference is now made to FIG. 3, which is a flowchart schematically illustrating a method for identifying transition points in a chemical reaction, according to an exemplary embodiment of the present invention.

According to an exemplary embodiment, an exemplary method for identifying transition points in a chemical reaction may be implemented using electric circuits, computer instructions, etc. The method may be implemented on a dedicated computer, on a computer chip connectable to a laboratory device (say to a PCR apparatus, as known in the art) or installable thereon, on a computerized controller (say a computerized controller used in a chemical factory), etc., as described in further detail hereinabove.

Optionally, the chemical reaction is a Polymerase Chain Reaction (PCR), say a Quantitative Fluorescent Polymerase Chain Reaction (QF-PCR).

In the exemplary method, there are received 310 values of a physical property of the chemical reaction, say by the physical property receiver 110, as described in further detail hereinabove.

Optionally, the physical property values are received from thermometric sensors installed inside a chamber where the chemical reaction takes place, from photometric sensors deployed in proximity to the chamber, or from other measurement devices, as described in further detail hereinabove.

For example, the chemical reaction may be a Quantitative Fluorescent Polymerase Chain Reaction (QF-PCR). The Quantitative Fluorescent Polymerase Chain Reaction is subjected to photometric measurements of light emitted from the QF-PCR reaction chamber, during the chemical reaction inside the QF-PCR chamber. The photometric measurement's values are then received 310, say by the property value receiver 110, as described in further detail hereinabove.

Next, there is calculated 320 a linear function connecting two of the received values. The two values pertain to a start and end of a time period, as described in further detail hereinbelow.

The time period may be a time period the chemical reaction is supposed to last for, a time period when a part of the chemical reaction takes place, a time period long enough for the reaction to happen, a time period spanning several cycles of the chemical reaction, etc.

Optionally, a user of the apparatus 1000 is allowed to define the start and end of the time period, say by inputting data defining the time period in absolute (say from 10:00 PM to 10:15 PM) or relative (say 15 minutes from start) terms.

Next, there is calculated 330 a difference between the linear function and two (or more) of the received values that pertain to the time period. For example, the difference calculator 130 may calculate 330 a differences between the linear function and a curve based on the receive values, over a time period of the chemical reaction (or a segment thereof), as described in further detail hereinbelow.

Finally, there is identified 340 one or more transition points of the chemical reaction, using the calculated difference, as described in further detail hereinbelow. For example, the transition point identifier 140 may identify 340 the transition points, by finding the points where the difference between the linear function and the received values is maximal, minimal, etc.

Optionally, at least one of the identified 340 transition points is a point in time of the chemical reaction, when the value of the physical property starts increasing substantially exponentially.

Optionally, at least one of the identified 340 transition points is a point in time of the chemical reaction, when the value of the physical property stops increasing substantially exponentially.

Optionally, at least one of the identified 340 transition points is a point in time of the chemical reaction, when the value of the physical property starts decreasing substantially exponentially.

Optionally, at least one of the identified 340 transition points is a point in time of the chemical reaction, when the value of the physical property stops decreasing substantially exponentially.

Optionally, when the transition point is identified 340, there is indicated a beginning of a phase of the chemical reaction, an end of a phase of the chemical reaction, an end of a preliminary stabilization phase of the chemical reaction, or any combination thereof.

Optionally, when the transition point is identified 340, there is initiated a control operation. The control operation may include, but is not limited to: initiating cooling of a chamber where the chemical reaction takes place, opening of a pressure valve of a reaction chamber, instructing a PCR Robot to stop rotating, etc., as known in the art.

Optionally, there is further generated monitoring data based on the identified transition point.

Optionally, the monitoring data is presented to a user. For example, the monitoring data may be presented on a computer screen, in an SMS (Short Messages Service) message on a cellular phone used by the user, in a message on a portable computer device such as a personal digital assistant (PDA), or a notebook computer, etc.

Reference is now made to FIGS. 4A, 4B, 4C, 4D and 4E, which are exemplary graphs, illustrating an exemplary scenario of identifying transition points in a chemical reaction, according to an exemplary embodiment of the present invention.

Figure 4A:
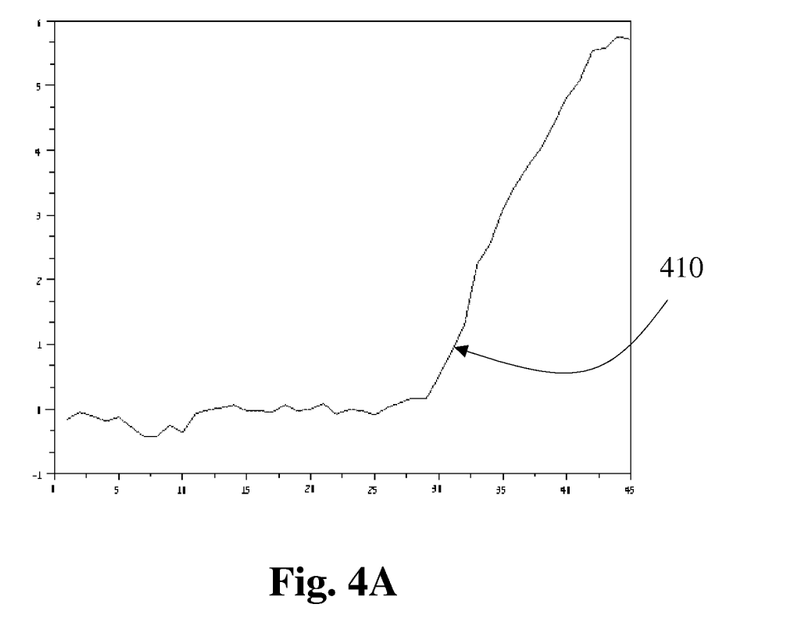
FIGS. 4A, 4B, 4C, 4D and 4E are exemplary graphs, illustrating an exemplary scenario of identifying transition points in a chemical reaction, according to an exemplary embodiment of the present invention.

FIG. 4A graphically shows an exemplary curve 410, which represents values measured during a time period of a chemical reaction (say values received using the property value receiver 110), as described in further detail hereinabove.

The x-axis corresponds to a time during the chemical reaction, whereas the y-axis represents the value of the property of the chemical reaction. That is to say that each point on curve 410 represents the property's value at a single point in time of the chemical reaction.

Figure 4B:
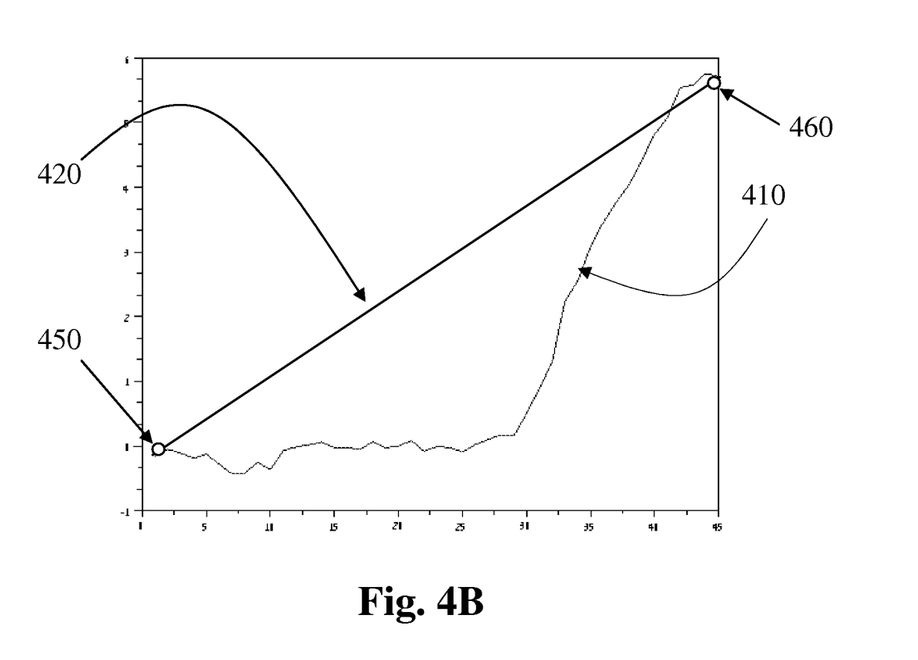

Reference is now made to FIG. 4B, which shows a curve of a first linear function 420, which connects a start point 450 and an end point 460 on curve 410. The first linear function 420 may be calculated by the linear function calculator 120, as described in further detail hereinabove.

Figure 4C:
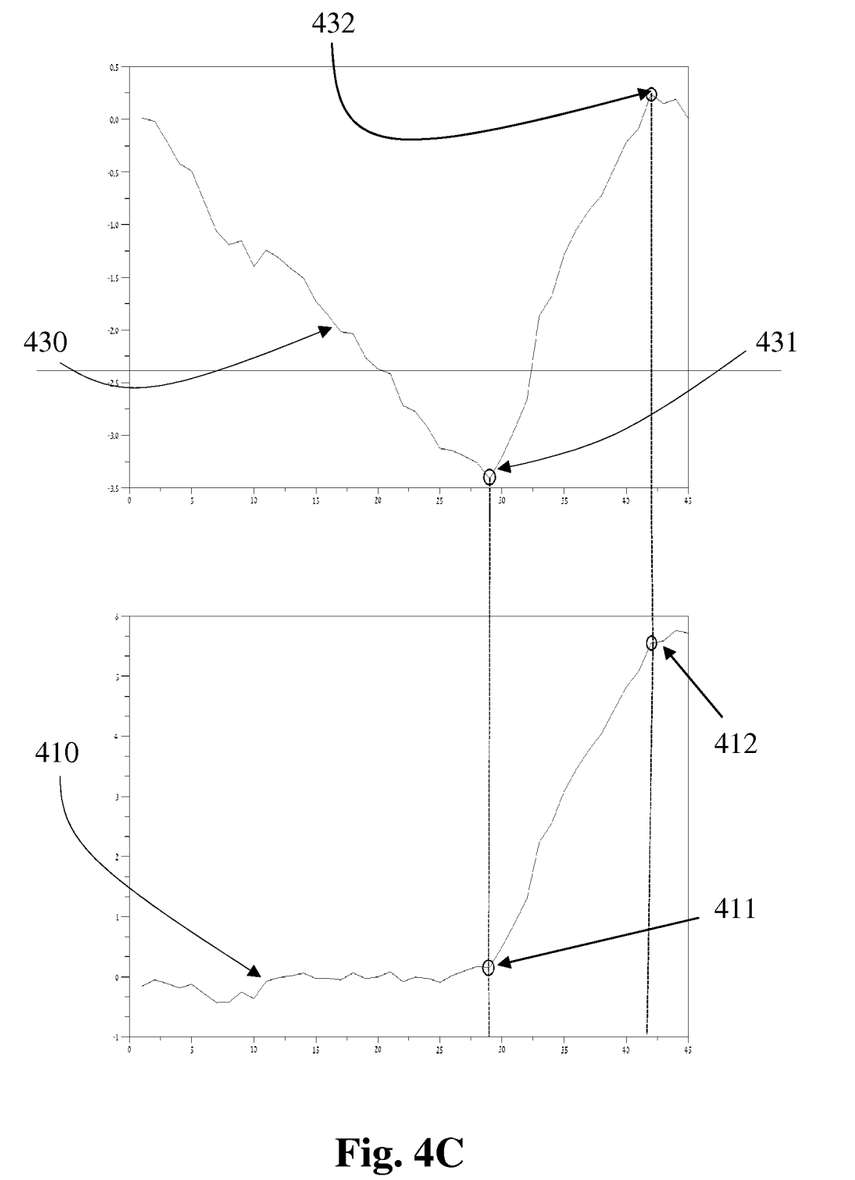

Reference is now made to FIG. 4C, which graphically shows a first difference curve 430. The first difference curve 430 represents the difference between the first linear function 420 and curve 410. That is to say that the difference curve 430 represents the difference between the first linear function 420 and the values of the physical property (say light emitted from a chemical chamber where the chemical reaction takes place) during the time period between the two points 450, 460.

Optionally, the difference represented by the first difference curve 430 is calculated by the difference calculator 130, as described in further detail hereinabove.

One or more extremum points of the difference curve 430, say a minimum point 431 and a maximum point 432, indicate the points in time of the chemical reaction (i.e. x-values) when transition points of the chemical reaction occur.

Consequently, points 411, 412 on curve 410, which correspond to the minimum point 431 and the maximum point 432, respectively, are identified as two transition points of the chemical reaction.

Optionally, in each of the transition points 411, 412, the value of the physical property starts decreasing substantially exponentially, stops decreasing substantially exponentially, starts increasing substantially exponentially, or stops increasing substantially exponentially, etc., as described in further detail hereinabove. That is to say that typically, in the transition point, the chemical reaction shifts from a substantially exponential phase into a substantially linear phase, or vise versa.

A method according to exemplary embodiment of the present invention may be applied on the whole chemical reaction (say on the whole of curve 410), and than on specific parts of the chemical reaction (say on certain intervals of the curve 410).

Figure 4D:
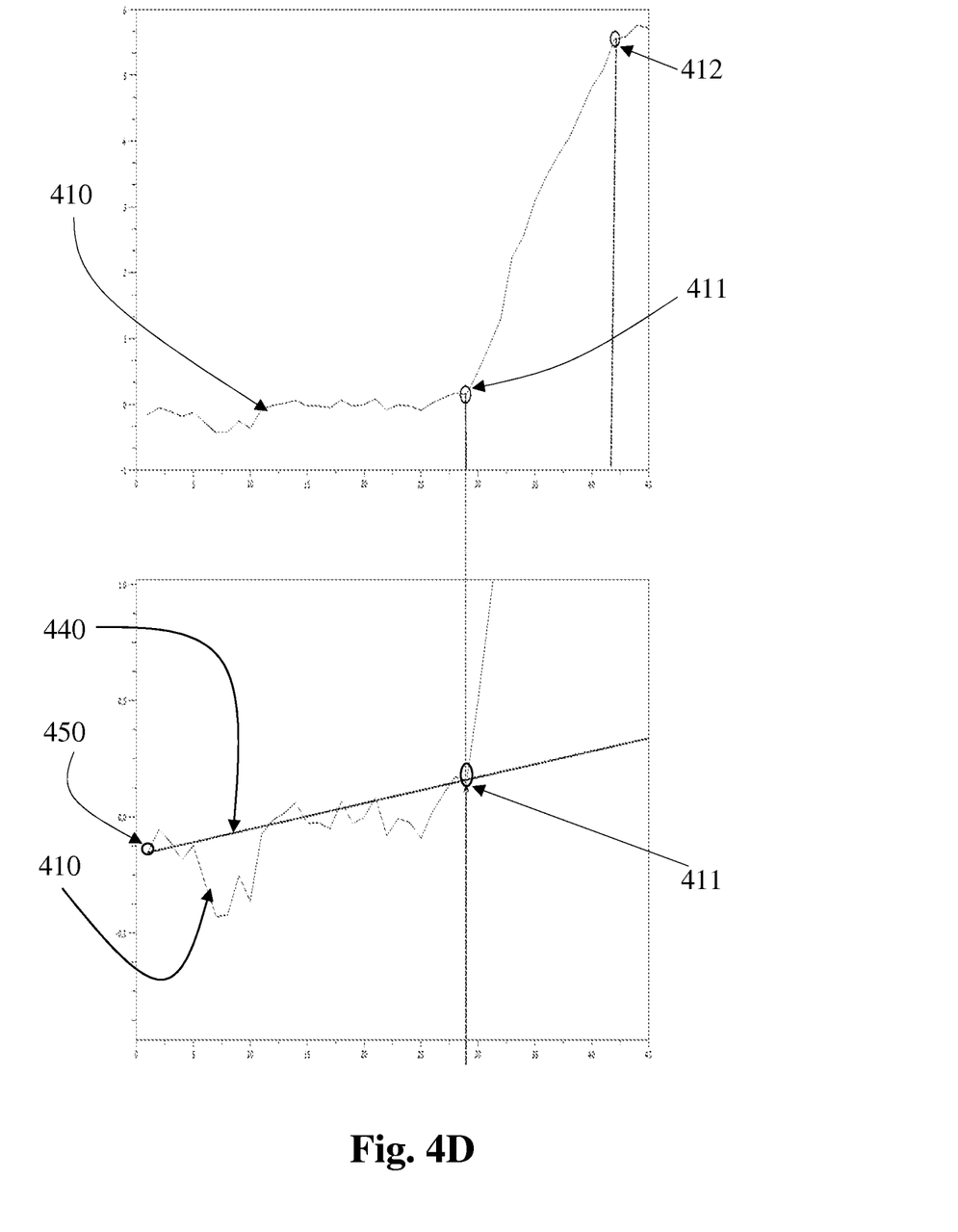

Reference is now made to FIG. 4D, which graphically shows a second linear function 440, which connects the first transition point 411 (which starts the exponential phase, which ends at the second transition point 412), and point 450.

The upper part of FIG. 4D shows curve 410 as it appears in FIG. 4A, whereas the lower part of FIG. 4D shows the curve 410 and the second linear function 440 in a co-ordinate system where the y-coordinate is re-scaled, so as to illustrate more clearly the initial part of the curve 410.

Figure 4E:
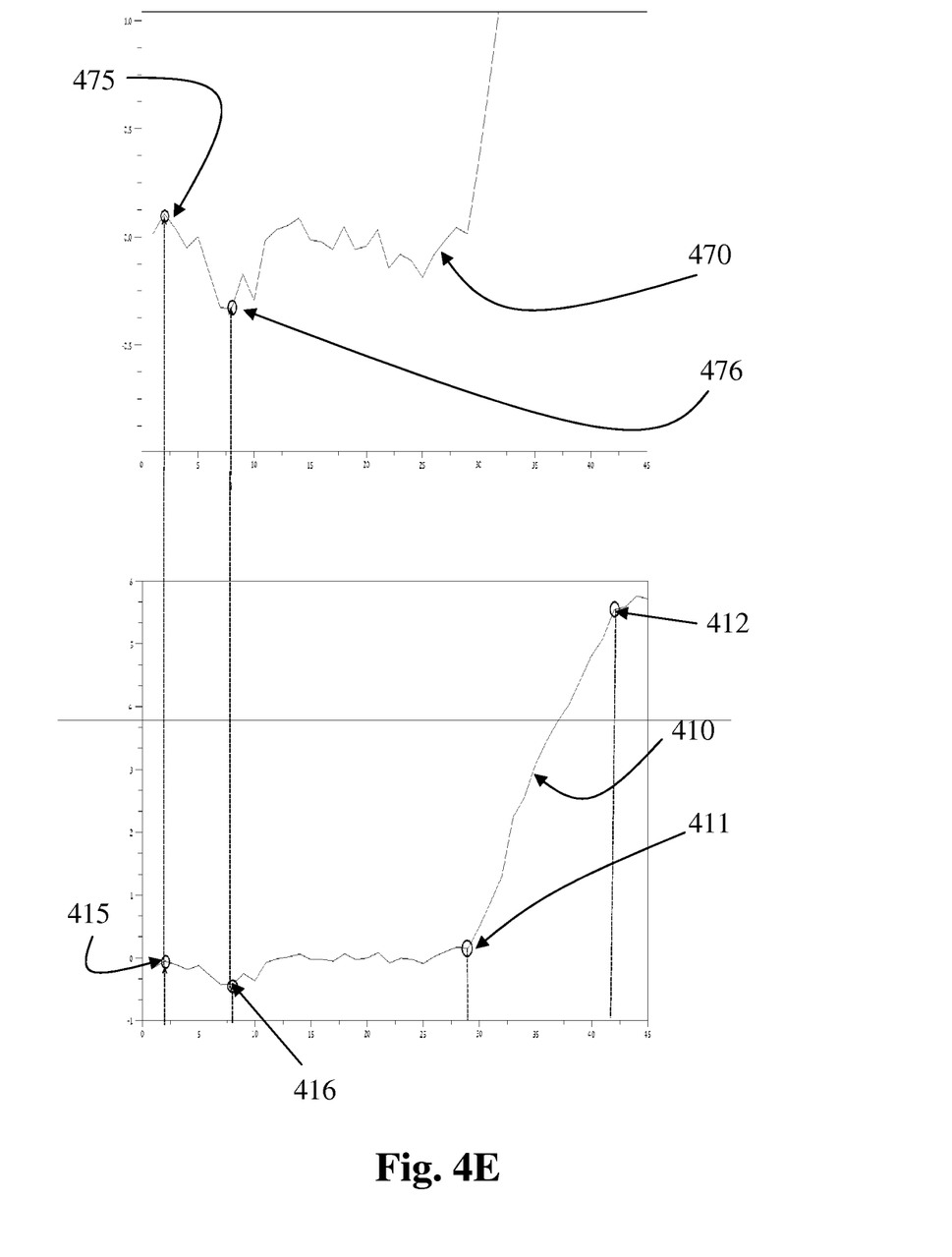

Reference is now made to FIG. 4E having a upper part which graphically shows a second difference curve 470 which represents the difference between the second linear curve and the received values (i.e. curve 410).

Optionally, the difference represented by the second difference curve 470 is calculated by the difference calculator 130, as described in further detail hereinabove.

The second difference function 470 has a maximum 475 and a minimum 476.

The maximum 475 and minimum 476 are used to identify the chemical reaction's transition points 415, 416, on curve 410, as shown in the lower part of FIG. 4E.

In one example, transition points 415 corresponds to a start of a preliminary phase where ingredients are added to the reaction, and cause the physical property's values (say light emitted from the chemical reaction's chamber) to fluctuate. Transition point 416 may correspond to a phase where the added ingredients reach an even distribution in the reaction chamber, which causes the physical property to stabilize.

Figure 5:
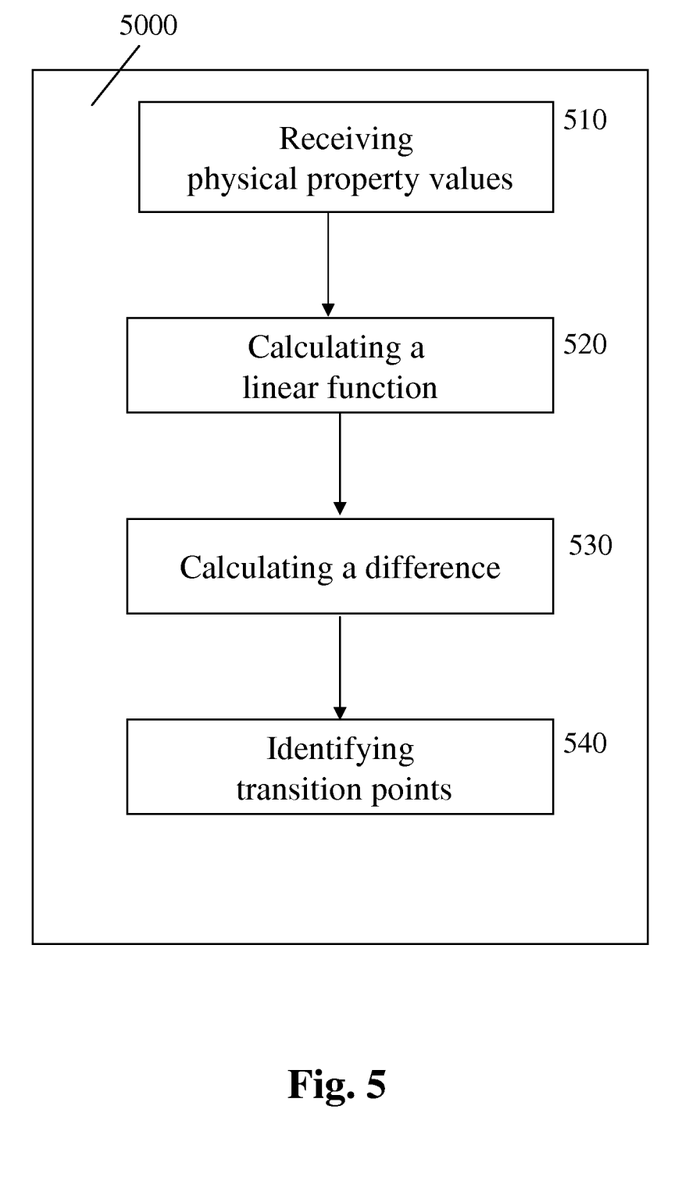
FIG. 5 is a block diagram schematically illustrating a computer readable medium storing computer executable instructions for performing steps of identifying transition points in a chemical reaction, according to an exemplary embodiment of the present invention.

Reference is now made to FIG. 5, which is a block diagram schematically illustrating a computer readable medium storing computer executable instructions for performing steps of identifying transition points in a chemical reaction, according to an exemplary embodiment of the present invention.

According to an exemplary embodiment of the present invention, there is provided a computer readable medium

5000 such as a CD-ROM, a USB-Memory, a Portable Hard Disk, a diskette, etc. The computer readable medium stores computer executable instructions, for performing steps of identifying transition points in a chemical reaction, according to an exemplary embodiment of the present invention.

Upon execution by a computer, the instructions receive 510 values of a physical property of the chemical reaction.

Optionally, the physical property values are received from thermometric sensors installed inside a chamber where the chemical reaction takes place, from photometric sensors deployed in proximity to the chamber, or from other measurement devices, as described in further detail hereinabove.

For example, the chemical reaction may be a Quantitative Fluorescent Polymerase Chain Reaction (QF-PCR). The Quantitative Fluorescent Polymerase Chain Reaction is subjected to photometric measurements of light emitted from the QF-PCR reaction chamber, during the chemical reaction inside the QF-PCR chamber. The photometric measurement's values are then received 510, as described in further detail hereinabove.

Then, the instructions calculate 520 a linear function connecting two of the received values. The two values pertain to a start and end of a time period, as described in further detail hereinbelow.

The time period may be a time period the chemical reaction is supposed to last for, a time period when a part of the chemical reaction takes place, a time period long enough for the reaction to happen, a time period spanning several cycles of the chemical reaction, etc.

Optionally, using some of the instructions, a user is allowed to define the start and end of the time period, say by inputting data defining the time period, as described in further detail hereinabove.

Next, the instructions calculate 530 a difference between the linear function and two (or more) of the received values that pertain to the time period. For example, the instructions may calculate a differences between the linear function and a curve based on the receive values, over a time period of the chemical reaction (or a segment thereof), as described in further detail hereinbelow.

Finally, the instructions identify 540 one or more transition points of the chemical reaction, using the calculated difference, as described in further detail hereinbelow. For example, the instructions may identify 540 the transition points, by finding the points where the difference between the linear function and the received values is maximal, minimal, etc.

Optionally, when the transition point is identified 540, the instructions further indicate that a phase of the chemical reaction begins, that a phase of the chemical reaction ends, that a preliminary stabilization phase of the chemical reaction ends, etc.

Optionally, when the transition point is identified 540, the instructions further initiate a control operation. The control operation may include, but is not limited to: initiating cooling of a chemical reaction chamber, opening of a pressure valve of a chemical reaction chamber, instructing a PCR Robot to stop rotating, etc.

Optionally, the instructions further generate monitoring data based on the identified transition point.

Optionally, the instructions further present the monitoring data to a user. For example, the monitoring data may be presented on a computer screen, in an SMS (Short Messages Service) message on a cellular phone used by the user, in a message on a portable computer device such as a personal digital assistant (PDA), or a notebook computer, etc.

It is expected that during the life of this patent many relevant devices and systems will be developed and the scope of the terms herein, particularly of the terms "Polymerase Chain Reaction", "Quantitative Fluorescent Polymerase Chain Reaction" and "Fluorescence", is intended to include all such new technologies a priori.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A polymerase chain reaction (PCR) reaction system comprising:
 a PCR reaction apparatus, comprising at least one sensor configured to measure a plurality of values of a physical property of a PCR process;
 an electronic computing device, in communication with said PCR reaction apparatus, configured to process data;
 a property value receiver, implemented at least in part on said electronic computing device, configured to receive the plurality of values of the physical property of the PCR process;
 a linear function calculator, associated with said property value receiver, configured to calculate a linear function spanning over at least a part of the PCR process, the at least a part of the PCR process spanning over a predefined time period having a start and end, the linear function connecting two of the received values, the two values pertaining to the start and end of the time period, the linear function having a first value pertaining to the start of the time period and being a same value as the received value pertaining to the start of the time period, and a second value pertaining to the end of the time period and being a same value as the received value pertaining to the end of the time period;
 a difference calculator, associated with said linear function calculator, configured to calculate a difference between the linear function and a plurality of the received values pertaining to the part; and
 a transition point identifier, associated with said difference calculator, configured to identify at least one transition point of the PCR process within the part, using the calculated difference; and
 a control operation initiator, associated with said transition point identifier, configured to initiate a control operation upon the transition point being identified.

2. The system of claim 1, wherein the values are photometric measurement values.

3. An apparatus for identifying transition points in a PCR process, the apparatus comprising:
- an electronic computing device configured to process data;
- a property value receiver, implemented at least in part on said electronic computing device, configured to receive a plurality of values of a physical property of the PCR process from a PCR reaction apparatus;
- a linear function calculator, associated with said property value receiver, configured to calculate a linear function spanning over at least a part of the PCR process, the at least a part of the PCR process spanning over a predefined time period having a start and end, the linear function connecting two of the received values, the two values pertaining to the start and end of the time period, the linear function having a first value pertaining to the start of the time period and being a same value as the received value pertaining to the start of the time period, and a second value pertaining to the end of the time period and being a same value as the received value pertaining to the end of the time period;
- a difference calculator, associated with said linear function calculator, configured to calculate a difference between the linear function and a plurality of the received values pertaining to the part;
- a transition point identifier, associated with said difference calculator, configured to identify at least one transition point of the PCR process within the part, using the calculated difference; and
- a control operation initiator, associated with said transition point identifier, configured to initiate a control operation upon the transition point being identified.

4. The apparatus of claim 3, wherein the values are photometric measurement values.

5. The apparatus of claim 3, wherein the values of the physical property start increasing substantially exponentially at the identified transition point.

6. The apparatus of claim 3, wherein the values of the physical property stop increasing substantially exponentially at the identified transition point.

7. The apparatus of claim 3, wherein the values of the physical property start decreasing substantially exponentially at the identified transition point.

8. The apparatus of claim 3, wherein the values of the physical property stop decreasing substantially exponentially at the identified transition point.

9. The apparatus of claim 3, further comprising a phase indicator, associated with said transition point identifier, configured to indicate a beginning of a phase of the PCR process upon the transition point being identified.

10. The apparatus of claim 3, further comprising a phase indicator, associated with said transition point identifier, configured to indicate an end of a phase of the PCR process upon the transition point being identified.

11. The apparatus of claim 3, further comprising a phase indicator, associated with said transition point identifier, configured to indicate an end of a preliminary stabilization phase of the PCR process upon the transition point being identified.

12. The apparatus of claim 3, further comprising a monitoring data generator, associated with said transition point identifier, configured to generate monitoring data based on the identified transition point of the PCR reaction apparatus.

13. The apparatus of claim 3, further comprising a measurement device, associated with said property value receiver, configured to measure the value of the physical property.

14. A computer implemented method for identifying transition points in a PCR process, the method comprising steps the computer is programmed to perform, the steps comprising:
a) receiving a plurality of values of a physical property of the PCR process from a PCR reaction apparatus;
b) calculating a linear function spanning over at least a part of the PCR process, the at least a part of the PCR process spanning over a predefined time period having a start and end, the linear function connecting two of the received values, the two values pertaining to the start and end of the time period, the linear function having a first value pertaining to the start of the time period and being a same value as the received value pertaining to the start of the time period, and a second value pertaining to the end of the time period and being a same value as the received value pertaining to the end of the time period;
c) calculating a difference between the linear function and a plurality of the received values pertaining to the part;
d) identifying at least one transition point of the PCR process within the part, using the calculated difference; and
e) initiating a control operation upon said identifying of the transition point.

15. The method of claim 14, wherein the values are photometric measurement values.

16. The method of claim 14, wherein the values of the physical property start increasing substantially exponentially at the identified transition point.

17. The method of claim 14, wherein the values of the physical property stop increasing substantially exponentially at the identified transition point.

18. The method of claim 14, wherein the value of the physical property starts decreasing substantially exponentially at the identified transition point.

19. The method of claim 14, wherein the values of the physical property stop decreasing substantially exponentially at the identified transition point.

20. The method of claim 14, further comprising indicating a beginning of a phase of the PCR process upon said identifying of the transition point.

21. The method of claim 14, further comprising indicating an end of a phase of the PCR process upon said identifying of the transition point.

22. The method of claim 14, further comprising indicating an end of a preliminary stabilization phase of the PCR process upon said identifying of the transition point.

23. The method of claim 14, further comprising generating monitoring data that is based on the identified transition point and presenting the monitoring data to a user of the PCR reaction apparatus.

24. The method of claim 14, further comprising measuring the value of the physical property.

25. A computer readable medium storing computer executable instructions for performing steps of identifying transition points in a PCR process, the steps comprising:
a) receiving a plurality of values of a physical property of the PCR process from a PCR reaction apparatus;
b) calculating a linear function spanning over at least a part of the PCR process, the at least a part of the PCR process spanning over a predefined time period having a start and end, the linear function connecting two of the received values, the two values pertaining to the start and end of the time period, the linear function having a first value pertaining to the start of the time period and being a same value as the received value pertaining to the start of the time period, and a second value pertaining to the end of the time period and being a same value as the received value pertaining to the end of the time period;

c) calculating a difference between the linear function and a plurality of the received values pertaining to the part;

d) identifying at least one transition point of the PCR process within the part, using the calculated difference; and e) initiating a control operation upon said identifying of the transition point.

26. The method of claim 14, further comprising instructing a robot based on the identified transition point.

\* \* \* \* \*